(12) United States Patent
Frey et al.

(10) Patent No.: US 7,692,052 B2
(45) Date of Patent: Apr. 6, 2010

(54) MULTI-ZONE PROCESS FOR THE PRODUCTION OF XYLENE COMPOUNDS

(75) Inventors: Stanley Frey, Palatine, IL (US); Gavin Towler, Inverness, IL (US)

(73) Assignee: UOP LLC, Des Plaines, IL (US)

( * ) Notice: Subject to any disclaimer, the term of this patent is extended or adjusted under 35 U.S.C. 154(b) by 342 days.

(21) Appl. No.: 11/763,235

(22) Filed: Jun. 14, 2007

(65) Prior Publication Data

US 2008/0161622 A1 Jul. 3, 2008

Related U.S. Application Data

(60) Provisional application No. 60/882,823, filed on Dec. 29, 2006.

(51) Int. Cl.
*C07C 6/12* (2006.01)
*C10G 35/06* (2006.01)

(52) U.S. Cl. .................. 585/319; 585/470; 208/133

(58) Field of Classification Search ................ 585/319, 585/470; 208/133

See application file for complete search history.

(56) References Cited

U.S. PATENT DOCUMENTS

| | | |
|---|---|---|
| 2,620,314 A | 12/1952 | Hoekstra |
| 2,892,858 A | 6/1959 | Ziegler |
| 3,130,006 A | 4/1964 | Rabo et al. |
| 3,308,069 A | 3/1967 | Wadlinger et al. |
| 3,702,292 A | 11/1972 | Burich |
| 3,702,886 A | 11/1972 | Argauer et al. |
| 3,709,979 A | 1/1973 | Chu |
| 3,832,449 A | 8/1974 | Rosinski et al. |
| 3,852,190 A | 12/1974 | Buss et al. |
| RE28,341 E | 2/1975 | Wadlinger et al. |
| 4,012,313 A | 3/1977 | Buss et al. |
| 4,076,842 A | 2/1978 | Plank et al. |
| 4,087,353 A | 5/1978 | Rausch |
| 4,150,061 A | 4/1979 | Feinstein et al. |
| 4,157,355 A | 6/1979 | Addison |
| 4,158,025 A | 6/1979 | Addison |
| 4,158,026 A | 6/1979 | Addison |
| 4,159,282 A | 6/1979 | Olson et al. |
| 4,163,018 A | 7/1979 | Tada et al. |
| 4,241,036 A | 12/1980 | Flanigen et al. |
| 4,278,565 A | 7/1981 | Chen et al. |
| 4,329,259 A | 5/1982 | Antos |
| 4,440,871 A | 4/1984 | Lok et al. |
| 4,537,754 A | 8/1985 | Casci et al. |
| 4,556,477 A | 12/1985 | Dwyer |
| 4,567,029 A | 1/1986 | Wilson et al. |
| 4,950,828 A | 8/1990 | Shum |
| 4,992,607 A | 2/1991 | Harandi et al. |

(Continued)

FOREIGN PATENT DOCUMENTS

WO 89/07586 8/1989

*Primary Examiner*—Thuan Dinh Dang
(74) *Attorney, Agent, or Firm*—David J. Piasecki

(57) ABSTRACT

A multi-zone process for the conversion of a hydrocarbon feedstock comprising cyclic compounds to produce aromatic compounds, and in particular xylene compounds. A naphtha boiling range stream having a boiling point range from about 71° C. (160° F.) to about 216° C. (420° F.) is reformed and/or transalkylated within reforming and transalkylation zones to produce an aromatics-rich high-octane stream containing xylene with increased xylene purity.

14 Claims, 1 Drawing Sheet

U.S. PATENT DOCUMENTS

| | | |
|---|---|---|
| 5,043,306 A | 8/1991 | Shum |
| 5,053,573 A | 10/1991 | Jorgensen et al. |
| 5,296,208 A | 3/1994 | Lesch |
| 5,347,061 A | 9/1994 | Harandi et al. |
| 5,396,010 A | 3/1995 | Harandi et al. |
| 5,406,016 A | 4/1995 | Cook et al. |
| 5,491,270 A | 2/1996 | Chin et al. |
| 5,599,439 A | 2/1997 | Collins et al. |
| 5,658,453 A | 8/1997 | Russ et al. |
| 5,723,710 A | 3/1998 | Gajda et al. |
| H1723 H | 4/1998 | Leuenberger et al. |
| 5,763,720 A | 6/1998 | Buchanan et al. |
| 6,004,452 A | 12/1999 | Ash et al. |
| 2005/0197518 A1 | 9/2005 | Miller et al. |

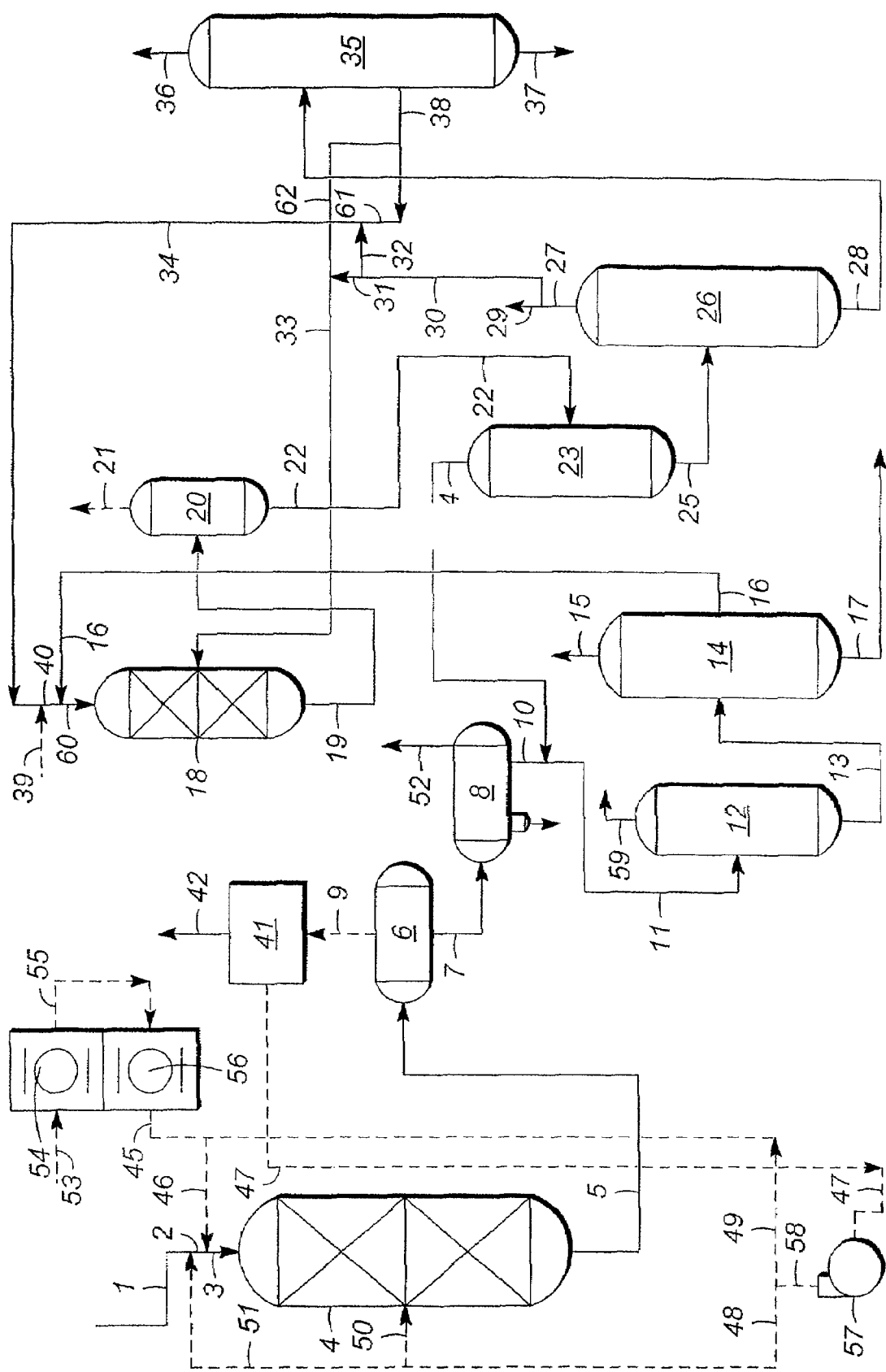

MULTI-ZONE PROCESS FOR THE PRODUCTION OF XYLENE COMPOUNDS

CROSS-REFERENCE TO RELATED APPLICATION

This application claims priority from Provisional Application No. 60/882,823 filed Dec. 29, 2006, the contents of which are hereby incorporated by reference.

FIELD

This invention generally relates to a process for the conversion of hydrocarbon feedstocks to produce aromatic compounds, and in particular xylene compounds, as well as low sulfur diesel and other hydrocarbon products.

BACKGROUND

It has been recognized that due to environmental concerns and newly enacted rules and regulations, saleable products must meet lower and lower limits on contaminants such as sulfur and nitrogen. Recently, new regulations require the essentially complete removal of sulfur from liquid hydrocarbons which are used in transportation fuels, such as gasoline and diesel.

Furthermore, there is increasing pressure to improve the quality of diesel fuel making it more difficult to blend light cycle oil (LCO) from a fluid catalytic cracking unit (FCC) into the diesel pool. Pressure to increase cetane number and reduce particulate emissions from diesel engines makes it more difficult to blend LCO, as the LCO stream contains a high proportion of aromatic compounds, naphthalenes, indanes, and tetralins, all of which have poor cetane numbers and tend to produce soot on burning. As the proportion of LCO that can be blended into diesel is reduced, the remainder must be blended into heavy fuel oil and as a result its value is substantially reduced.

An alternative means for using LCO is to subject it to mild hydrocracking to improve the product quality. Hydrocracking of LCO produces an aromatic-rich gasoline stream of higher octane than would normally be obtained from hydrocracking, together with a distillate stream of improved cetane number. In some refineries configured for petrochemical production, it may be desirable to carry out additional processing to maximize the yield of valuable xylenes from the aromatic gasoline produced in the LCO hydrocracker.

The xylene isomers are produced in large volumes from petroleum as feedstocks for a variety of important industrial chemicals. The most important of the xylene isomers is par-axylene, the principal feedstock for polyester which continues to enjoy a high growth rate from a large base demand. Orthoxylene is used to produce phthalic anhydride, which has high-volume but mature markets. Metaxylene is used in lesser but growing volumes for such products as plasticizers, azo dyes and wood preservers. Ethylbenzene generally is present in xylene mixtures and is occasionally recovered for styrene production, but usually is considered a less desirable component of C8 aromatics.

Among the aromatic hydrocarbons, the overall importance of the xylenes rivals that of benzene as a feedstock for industrial chemicals. The xylenes are not directly recovered from petroleum by the fractionation of naphtha in sufficient volume to meet demand nor in a high enough purity; thus conversion of other hydrocarbons is necessary to increase the purity and yield of the xylenes. For straight run naphtha feedstocks, which may be naphtha distilled out of crude oil, it is necessary to utilize high severity reforming with inter-reactor reheat to convert large amounts of paraffins, such as from about 40 to about 70 weight percent, and having about 30 to about 60% total cyclic content, to the desired xylenes and/or benzene. Moreover, the large amount of non-aromatic content remaining in the reformed naphtha requires substantial subsequent processing to remove the non-aromatics and to transalkylate the aromatics to benzene and xylene.

Heretofore where just the non-xylene co-boiling feedstock streams having C7 and C9/C10 cuts from naphtha might be fed to a transalkylation zone and xylene co-boiling streams containing C8 cuts in the naphtha may be bypassed from the transalkylation zone and fed directly to a product xylene column, the xylene product purity becomes low, i.e., less than 80% xylene content.

SUMMARY

The present method and processing apparatus provide for reforming and/or transalkylating a full cut hydrocracked naphtha stream, including xylene co-boiling non-aromatic streams, having at least about 80% cyclics, less than about 40% naphthenes, and less than about 20% paraffins and typically boiling in the range from about 71° C. (160° F.) to about 216° C. (420° F.), rather than reforming and/or transalkylating just non-xylene co-boiling streams. By also feeding the xylene co-boiling non-aromatics from a full cut hydrocracked naphtha into the reforming and/or transalkylation zones, a higher purity of xylenes is achieved (i.e., at least greater than about 90%) and the total yield of xylenes is not significantly affected. Furthermore, the present method may reduce the reforming zone to a single reactor, followed by a transalkylation zone with a cracking function for feed streams with low paraffin content, low naphthene content and high aromatic content.

In one aspect, the present invention provides a process for the production of xylenes from a hydrocarbonaceous feedstock subject to mild hydrocracking, the xylene stream having improved purity with little, if any, significant yield loss. In this aspect, the process comprises providing a hydrocarbonaceous feedstock stream containing a significant amount of multi-ring aromatic compounds and cyclic paraffins, and passing the feedstock stream into a main fractionation zone wherein the stream is separated into at least a naphtha stream boiling in the range from about 71° C. (160° F.) to about 216° C. (420° F.), and one other stream, where the other stream may comprise a light naphtha stream for blending directly into gasoline and boiling below about 91° C. (195° F.), or more preferably below about 71° C. (160° F.). The naphtha stream comprising a significant amount of mid-cut hydrocarbons, such as C7 to C9 hydrocarbons, typically having seven (C7) and eight (C8) carbon numbers, may also include C9 aromatics and naphthenes (and may also include heavy-cut hydrocarbons, such as C9 and C10 aromatics).

The naphtha stream is introduced into a transalkylation zone, and at least a portion of the stream is contacted with a transalkylation catalyst, under transalkylation conditions, to produce a liquid hydrocarbonaceous effluent that is recovered into xylenes and a gaseous stream comprising hydrogen. The recovered amount of xylenes after transalkylation is greater than the xylene content of the naphtha stream before the naphtha stream contacts the transalkylation catalyst. In another aspect, prior to feeding the stream into the transalkylation zone the xylene co-boiling non-aromatics from the naphtha stream may be introduced into a reforming zone to increase the aromatic hydrocarbon content of the naphtha stream. The fraction of the naphtha stream from the transalkylation zone having the increased xylene content is then separated from the other fractions comprising the stream.

In this aspect, some of the C7-C10 non-aromatics (i.e., naphthenes) may be converted into aromatics in the reforming zone and the remaining C7-C10 non-aromatics may be cracked to liquid petroleum gas (LPG) range composition in the transalkylation zone. In yet another aspect, a naphtha stream feedstock has at least about 75% cyclic compounds, and the naphtha stream has a boiling point from about 71° C. (160° F.) to about 216° C. (420° F.), with less than about 40% naphthenes.

In one aspect of the process, the total yield of the fraction having xylene co-boiling fractions is not significantly reduced, if at all, by the separation and conversion of the selected naphtha stream from the feedstock. But the purity of the resulting xylene stream is improved substantially, and in some aspects, may achieve purity levels of approximately 90% or higher, or preferably about 95% or higher, or still preferably about 98% or higher. In such aspects of the process, the yield of C6 and C8 aromatics may be increased and the C7 aromatics may be reacted with C9 aromatics in the transalkylation step to produce additional mixed xylenes providing yield and purity improvements.

In another aspect, the hydrocarbonaceous feedstock may be separated in the fractionation zone into at least a fraction stream comprising a light hydrocarbon stream boiling below about 91° C. (195° F.) and a fraction stream comprising a hydrocarbon stream boiling above about 193° C. (380° F.), and comprising a significant amount of ultra low sulfur diesel. Optionally, a selected naphtha stream having a boiling range of about 71° C. (160° F.) to about 216° C. (420° F.) may be introduced into a reforming zone prior to the transalkylation zone. In this aspect, the naphtha stream may be contacted with a reforming catalyst in a single reactor without inter-reactor reheat under reforming conditions to produce an effluent that is then passed into the transalkylation zone. In yet another aspect, all or part of the naphtha stream may partially bypass the reforming zone and a portion of the naphtha stream is introduced directly into the transalkylation zone. Hydrogen produced in the reforming zone is separated from the transalkylation effluent.

In another aspect, the hydrocarbonaceous feedstock may originate from a hydrocracking zone where it is hydrocracked. The effluent from the hydrocracking zone is separated to produce a stream comprising hydrogen and the naphtha stream having a boiling point of about 71° C. (160° F.) to about 216° C. (420° F.), where this naphtha stream has less than about 40% of naphthenes and is passed into the reforming/transalkylation zone to provide an improved purity xylene stream.

BRIEF DESCRIPTION OF THE DRAWING

The drawing is a simplified process flow diagram of a preferred embodiment of the process and processing apparatus described herein. The above described drawing is intended to be schematically illustrative of the process and apparatus and is not to be a limitation of any invention.

DETAILED DESCRIPTION

The process and processing apparatus described herein are particularly useful for the production of xylene from a hydrocarbon feedstock. Suitable hydrocarbon feedstocks boil in the range from about 149° C. (300° F.) to about 399° C. (750° F.) and preferably contain at least about 50 vol-% aromatic compounds. Particularly preferred feedstocks contain at least a portion of light cycle oil (LCO), which is a by-product of fluid catalytic cracking (FCC) processes, as used in the production of hydrocarbonaceous products. LCO is an economical and advantageous feedstock as it typically is not considered a finished product and contains significant quantities of sulfur, nitrogen and polynuclear aromatic compounds. Therefore, the process and processing apparatus permit the conversion of a relatively low-value LCO stream into valuable xylene hydrocarbon compounds, low sulfur diesel products, gasoline products, and/or other hydrocarbon products. Other possible feedstocks may be used that comprise cracked naphtha from any other cracking process (i.e., hydrocracking, FCC, thermal cracking) to produce a desired paraffin, naphthene and cyclic content range.

In one aspect, the feedstock is separated, typically in a main fractionation zone, into at least a single fraction stream, or a main naphtha stream (typically by distillation), having a boiling point range of about 71° C. (160° F.) to about 216° C. (420° F.). Alternatively, the main fractionation zone may separate the feedstock stream into one or more additional fraction streams with higher or lower boiling point ranges. Although sending the entire naphtha stream including the C8 cut to the transalkylation zone may lose some of the total liquid yield due to the transalkylation zone being an equilibrium-limited reactor, the high level of purity of xylenes achieved proves to outweigh the minimal loss in total liquid yield. The process and apparatus provide higher purity xylene products and, while not intending to be bound by any theory, this may be because any naphthenes present may be converted into aromatics, the yield of C7 and C8 aromatics can thereby be increased, and the C7 aromatics can be reacted with the C9 aromatics in the transalkylation zone to produce additional mixed xylenes.

In one aspect of the process, the main fractionation zone may separate the feedstock stream into at least three fractions of different boiling point ranges. A first fraction may comprise a light naphtha stream boiling at temperatures below about 126° C. (260° F.) suitable for blending directly to gasoline. In another aspect, the first fraction may comprise a light naphtha stream boiling at temperatures below about 91° C. (195° F.), and more preferably below about 71° C. (160° F.). This stream typically comprises benzene and does not contain substantial amounts of C7 naphthenes or toluene. Alternatively, where it is desirable to reduce the amount of benzene in the first fraction, the cut point for that fraction may be decreased to about 71° C. (160° F.).

A main naphtha stream, or second fraction, may be selected with a boiling range of about 71° C. (160° F.) to about 216° C. (420° F.), and comprises primarily mid-cut hydrocarbon naphthas, such as C7 to C9 hydrocarbons (and may also include heavy-cut naphthas, such as C9 and C10 hydrocarbons). Alternatively, where the first fraction boils below the higher boiling temperature of 126° C. (260° F.), then the second fraction may be selected with a boiling range of about 126° C. (260° F.) to about 216° C. (420° F.). In one aspect, the stream may comprise substantially all of the C7 and C8 compounds from the feedstock stream, substantially all of the C9 and C10 aromatic compounds, and substantially all of the C9 naphthenes (if any are present). The C8 compounds of the main naphtha stream include xylenes, the xylene content generally comprising greater than about 3 weight % in the main naphtha stream. In another aspect, the xylene content of the main naphtha stream is greater than about 5 weight %, and in still another aspect the xylene content of the main naphtha stream is greater than about 10 weight %. In one such aspect, a fresh naphtha stream may be used, i.e., without a recycled naphtha content, and the xylene content of the fresh naphtha stream may be at least about 5 weight % and, in another such aspect, may be about 20 weight % of the stream.

The composition of the second fraction will depend on the composition of the feedstock, as well as the desired composition of the second fraction for a particular application. The selected boiling range, for example, may be decreased or increased for specific applications, to provide different mixes of aromatics and naphthenes (i.e., non-aromatic ring compounds). In one aspect, the main naphtha stream has less than about 40% naphthenes, such as in a range of about 10 to about 40%, and preferably in a range of about 15 to about 30%, and has less than about 20% paraffins, and preferably less than about 15% paraffins.

A third fraction may be selected from the feedstock comprising an ultra-low sulfur diesel stream boiling at temperatures greater than about 193° C. (380° F.), and more preferably boiling above about 216° C. (420° F.). The ultra-low sulfur diesel stream may be recovered, or optionally recycled to be re-processed and again passed through the main fractionation column after a possible additional processing step, such as hydrocracking.

In yet another aspect, the main naphtha stream comprises mid-cut naphthas and also heavy-cut naphthas with a boiling point range from about 71° C. (160° F.) to about 216° C. (420° F.) and may be further separated into a mid-cut naphtha stream and a separate heavy-cut naphtha stream. In this aspect, the mid-cut naphtha stream may have a temperature range of about 71° C. (160° F.) to about 176° C. (350° F.), and may comprise substantially all of the C7 and C8 compounds, and most of the C9 aromatics and C9 naphthenes, if any are present, from the feedstock stream. The heavy-cut naphtha stream may have a temperature range of about 176° C. (350° F.) to about 216° C. (420° F.), and may comprise C9 and C10 aromatic compounds. In this aspect, the mid-cut naphtha stream may be introduced into a reforming/transalkylation zone (discussed below), and the heavy-cut naphtha stream may be introduced into a reforming/transalkylation zone or may be introduced directly into the xylene product column (discussed below). The third fraction of ultra-low sulfur diesel stream would then comprise a stream boiling at temperatures greater than about 204° C. (400° F.), and preferably above about 216° C. (420° F.).

In one aspect, the main naphtha stream from the main fractionation zone is fed to a reforming zone. The main naphtha stream has less than about 40% naphthenes content and less than about 20% paraffin content, preferably less than about 15%, and the stream going into the main fractionation zone has at least about 80% cyclic compounds, and preferably at least about 85%. In this aspect, it is preferred to limit the amount of non-cyclic compounds in the main naphtha stream to improve the liquid product yields and minimize hydrogen consumption.

In another aspect, a stream containing C9 and C10 aromatics selected from a final fractionation zone bottoms stream (i.e., xylene column), to be discussed herein below, may be fed into a reformer reactor/transalkylation zone or may bypass the reforming zone and go straight to a transalkylation zone. Furthermore, if the main fractionation zone separates the mid- and heavy-cut naphtha streams into two streams, then the heavy naphtha stream, comprising mostly C9 and C10 aromatics, may be combined with a bottoms stream from a toluene column or with a bottoms stream from a xylene column and recycled back to the reforming/transalkylation zones.

In the reforming zone, the naphtha stream and a hydrogen-rich gas may be preheated and charged to a reaction zone containing typically one reactor. However, other reactor configurations may be used to achieve similar results. The reactants may contact the catalyst in the individual reactors in upflow, downflow, or radial flow fashion. The catalyst may be contained in a fixed-bed system or in a moving-bed system with associated continuous catalyst regeneration. Alternative approaches to reactivation of deactivated catalyst are well known to those skilled in the art, and include semi-regenerative operation in which the entire unit is shut down for catalyst regeneration and reactivation or swing-reactor operation in which an individual reactor is isolated from the system, regenerated and reactivated while the other reactors remain on-stream.

The hydrogen make-up gas introduced to the reforming zone may preferably contain at least 70% pure hydrogen gas. After flowing through the transalkylation zone, the hydrogen-rich gas may be separated and recycled or may be separated and recovered. This may typically be done by using a second separator downstream of the transalkylation zone, as discussed herein.

Reforming conditions applied in the reforming zone of the present invention may include a pressure selected within the range of about 700 kPa (100 psig) to about 7 MPa (1000 psig), and preferably to about 3.5 MPa (500 psig). Particularly good results are obtained at low pressure, namely a pressure of about 350 kPa (50 psig) to about 2750 kPa (400 psig). Reforming temperature may be in the range from about 300° C. (572° F.) to about 565° C. (1049° F.). Sufficient hydrogen is supplied to thereby provide an amount of about 1 to about 20 moles of hydrogen per mole of hydrocarbon feed entering the reforming zone, with excellent results being obtained when about 2 to about 10 moles of hydrogen are used per mole of hydrocarbon feed. Likewise, the liquid hourly space velocity used in reforming may be selected from the range of about 0.2 to about 20 $hr^{-1}$.

The reforming zone and transalkylation zone may contain one or more beds of the same or different catalyst, and such beds may be disposed in one or more vessels. The zones may be integrated together in connected serial processes using multiple vessels or directly coupled together. An integrated reforming-transalkylation zone may contain one or more vessels or beds each containing one or more types of reforming catalyst and/or transalkylation catalyst. Such types of catalyst are segregated with dual catalytic functions composited on the same particles.

The hydrogen containing effluent stream from the reforming zone may be introduced into the transalkylation zone. Additional hydrogen may be added to the transalkylation zone and preferably contains at least 70 mol-% hydrogen with essentially no hydrogen sulfide or ammonia. Operating conditions preferably employed in the integrated reforming-transalkylation zone normally may include a temperature from about 300° C. (572° F.) to about 550° C. (1022° F.) and a liquid hourly space velocity in the range from about 0.2 to about 10 $hr^{-1}$.

In the transalkylation zone, the combined feedstock may preferably be transalkylated in the vapor phase and in the presence of hydrogen. The effluent from the reforming zone contains less than about 20% non-aromatics of the C6+ component in the effluent. Aromatic C9 hydrocarbons and above, originating from the bottoms stream of the xylene product column (discussed below), may also be fed directly to the transalkylation zone and thus bypass the reforming zone. This heavy aromatic stream bypass can also be used as a heat sink to control any temperature differential needed between the reforming zone outlet and transalkylation zone inlet. If feedstock is transalkylated in the liquid phase, then the presence of hydrogen is optional. If present, free hydrogen is associated with the feedstock and recycled hydrocarbons in an amount of from about 0.1 moles per mole of hydrocarbon up to 10 moles per mole of hydrocarbon. This may be referred to as a hydrogen to hydrocarbon ratio. The transalkylation reaction preferably yields a product having increased xylene content and also comprising toluene. In one aspect, the transalkylation zone has an accompanying non-aromatic cracking function which removes the benzene to A9 boiling range non-aromatics. These non-aromatics are cracked to LPG range material allowing for high purity benzene or xylene product from the downstream fractionation zone.

The feed to the transalkylation reaction zone first may need to be cooled, since the effluent from the reforming zone will typically be at a higher temperature than desired. The reforming effluent stream is typically cooled by combining it with a colder C9/C10 or toluene recycle stream. The feed then may be passed through a reaction zone, which may comprise one or more individual reactors. The use of a single reaction vessel having a fixed cylindrical bed of transalkylation catalyst is preferred, but other reaction configurations utilizing moving beds of catalyst or radial-flow reactors may be employed if desired. Passage of the combined feed through the reaction zone effects the production of an effluent stream comprising unconverted feed and product hydrocarbons. This effluent may normally be cooled by indirect heat exchange against the stream entering the reaction zone and then further cooled through the use of air or cooling water. The effluent may then be passed into a fractionation column, or a series of fractionation columns (i.e., a benzene column, and then a toluene column). Optionally, the feed may be heated if too cold to reach the desired temperature by indirect heat exchange against the effluent of the reaction zone and then may be heated to reaction temperature by exchange with a warmer stream, steam or a furnace.

To effect a transalkylation reaction, the present invention may incorporate a transalkylation catalyst in at least one zone, but no limitation is intended in regard to a specific catalyst. Conditions employed in the transalkylation zone may normally include a temperature of from about 300° C. (572° F.) to about 540° C. (1004° F.). The transalkylation zone may be operated at moderately elevated pressures broadly ranging from about 100 kPa (14.7 psig) to about 6 MPa (870 psig). The transalkylation reaction can be effected over a wide range of space velocities. Liquid hourly space velocity generally ranges from about 0.1 to about 20 $hr^{-1}$.

It is a preferred practice to operate the reforming zone of the present invention in a substantially sulfur-free environment. Any guard bed control means known in the art may be used to treat the naphtha feedstock which is to be charged to the reforming reaction zone. For example, the feedstock may be subjected to guard bed adsorption processes, guard bed catalytic processes, or combinations thereof. Preferred guard bed adsorption processes may employ adsorbents such as molecular sieves, high surface area aluminas, high surface area silica-aluminas, carbon molecular sieves, crystalline aluminosilicates, activated carbons, and high surface area metallic containing compositions, such as nickel or copper and the like. Guard beds may be loaded in separate vessels in the reforming zone or the hydrocracking zone, or guard beds may be loaded inside the catalyst vessel or vessels themselves. Guard beds may also be loaded in conjunction with the transalkylation zone as needed to deal with any contaminants such as sulfur or chloride that may arise from specific streams passing over the transalkylation catalyst. However, some amount of sulfur is needed to control production of coke catalyzed from the metal walls of the vessels and may be re-injected into the system at about 0.5 ppm.

Any suitable reforming catalyst may be utilized in the reforming zone. Preferred reforming catalysts contain a solid refractory oxide support having dispersed thereon at least one platinum group metal component and optionally a modifier metal component such as tin or rhenium. The support can be any of a number of well-known supports in the art including aluminas, silica/alumina, silica, titania, zirconia, and zeolites. The aluminas which can be used as support include gamma alumina, theta alumina, delta alumina, and alpha alumina with gamma and theta alumina being preferred. Included among the aluminas are aluminas which contain modifiers such as tin, zirconium, titanium and phosphate. The zeolites which can be used include: faujasites, zeolite beta, L zeolite, ZSM 5, ZSM 8, ZSM 11, ZSM 12 and ZSM 35. The supports can be formed in any desired shape such as spheres, pills, cakes, extrudates, powders, granules, etc. and they may be utilized in any particular size.

One way of preparing a spherical alumina support is by the well known oil drop method which is described in U.S. Pat. No. 2,620,314. The oil drop method comprises forming an aluminum hydrosol by any of the techniques taught in the art and preferably by reacting aluminum metal with hydrochloric acid; combining the hydrosol with a suitable gelling agent; and dropping the resultant mixture into an oil bath maintained at elevated temperatures. The droplets of the mixture remain in the oil bath until they set and form hydrogel spheres. The spheres are then continuously withdrawn from the oil bath and typically subjected to specific aging and drying treatments in oil and ammoniacal solutions to further improve their physical characteristics. The resulting aged and gelled spheres are then washed and dried at a relatively low temperature of about 80° to 260° C. and then calcined at a temperature of about 455° to 705° C. for a period of about 1 to about 20 hours. This treatment effects conversion of the hydrogel to the corresponding crystalline gamma alumina. If theta alumina is desired then the hydrogel spheres are calcined at a temperature of about 950° to about 1100° C.

An alternative form of carrier material may be cylindrical extrudate, preferably prepared by mixing the alumina powder with water and suitable peptizing agents such as HCl until an extrudable dough is formed. The resulting dough may be extruded through a suitably sized die to form extrudate particles. These particles are then dried at a temperature of about 260° to about 427° C. for a period of about 0.1 to 5 hours to form the extrudate particles. It is preferred that the refractory inorganic oxide comprises substantially pure alumina. A typical substantially pure alumina has been characterized in U.S. Pat. No. 3,852,190 and U.S. Pat. No. 4,012,313 as a by-product from a Ziegler higher alcohol synthesis reaction as described in Ziegler's U.S. Pat. No. 2,892,858.

An essential ingredient of the reforming catalyst may be a dispersed platinum-group component. This platinum-group component may exist within the final catalytic composite as a compound such as an oxide, sulfide, halide, oxyhalide, etc., in chemical combination with one or more of the other ingredients of the composite or as an elemental metal. It is preferred that substantially all of this component may be present in the elemental state and may be uniformly dispersed within the support material. This component may be present in the final catalyst composite in any amount which is catalytically effective, but relatively small amounts are preferred. Of the platinum-group metals which can be dispersed on the desired support, preferred metals are rhodium, palladium, platinum, and platinum being most preferred.

A Group IVA (IUPAC 14) metal component may be an optional ingredient of the reforming catalyst. Of the Group IVA (IUPAC 14) metals, germanium and tin are preferred and tin is especially preferred. This component may be present as an elemental metal, as a chemical compound such as the oxide, sulfide, halide, oxychloride, etc., or as a physical or chemical combination with the porous carrier material and/or other components of the catalytic composite. Preferably, a substantial portion of the Group IVA (IUPAC 14) metal exists in the finished catalyst in an oxidation state above that of the elemental metal.

Rhenium may also be an optional metal promoter of the reforming catalyst. In addition to the catalytic components described above, other components may be added to the catalyst. For example, a modifier metal selected from the non-exclusive list of lead, indium, gallium, iridium, lanthanum, cerium, phosphorous, cobalt, nickel, iron and mixtures thereof may be added to the reforming catalyst.

Another optional component of the reforming catalyst, particularly useful in embodiments of the present invention comprising dehydrogenation, dehydrocyclization, or hydrogenation reactions, may be an alkali or alkaline-earth metal component. More precisely, this optional ingredient may be selected from the group consisting of the compounds of the alkali metals—cesium, rubidium, potassium, sodium, and lithium—and the compounds of the alkaline earth metals—calcium, strontium, barium, and magnesium.

Any suitable transalkylation catalyst may be utilized in the transalkylation zone. Preferred transalkylation catalysts contain a solid-acid material combined with an optional metal component. Suitable solid-acid materials include all forms and types of mordenite, mazzite (omega zeolite), beta zeolite, ZSM-5, ZSM-11, ZSM-12, ZSM-22, ZSM-23, MFI type zeolite, NES type zeolite, EU-1, MAPO-36, MAPSO-31, SAPO-5, SAPO-11, SAPO-41, and silica-alumina or ion exchanged versions of such solid-acids. For example, in U.S. Pat. No. 3,849,340 a catalytic composite is described comprising a mordenite component having an $SiO_2/Al_2O_3$ mole ratio of at least 40:1 prepared by acid extracting $Al_2O_3$ from mordenite prepared with an initial $SiO_2/Al_2O_3$ mole ratio of less than 30:1 and a metal component selected from copper, silver and zirconium. Refractory inorganic oxides, combined with the above-mentioned and other known catalytic materials, have been found useful in transalkylation operations.

For instance, silica-alumina is described in U.S. Pat. No. 5,763,720. Crystalline aluminosilicates have also been employed in the art as transalkylation catalysts. ZSM-12 is more particularly described in U.S. Pat. No. 3,832,449. Zeolite beta is more particularly described in Re. 28,341 (of original U.S. Pat. No. 3,308,069). A favored form of zeolite beta is described in U.S. Pat. No. 5,723,710, which is incorporated herein by reference. The preparation of MFI topology zeolite is also well known in the art. In one method, the zeolite may be prepared by crystallizing a mixture containing an alumina source, a silica source, an alkali metal source, water and an alkyl ammonium compound or its precursor.

Further descriptions are in U.S. Pat. No. 4,159,282, U.S. Pat. No. 4,163,018, and U.S. Pat. No. 4,278,565. The synthesis of the Zeolite Omega is described in U.S. Pat. No. 4,241,036. ZSM intermediate pore size zeolites useful in this invention include ZSM-5 (U.S. Pat. No. 3,702,886); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842). European Patent EP 0378916 B1 describes NES type zeolite and a method for preparing NU-87. The EUO structural-type EU-1 zeolite is described in U.S. Pat. No. 4,537,754. MAPO-36 is described in U.S. Pat. No. 4,567,029. MAPSO-31 is described in U.S. Pat. No. 5,296,208 and typical SAPO compositions are described in U.S. Pat. No. 4,440,871 including SAPO-5, SAPO-11 and SAPO-41.

A refractory binder or matrix may optionally be utilized to facilitate fabrication of the transalkylation catalyst, provide strength and reduce fabrication costs. The binder should be uniform in composition and relatively refractory to the conditions used in the process. Suitable binders include inorganic oxides such as one or more of alumina, magnesia, zirconia, chromia, titania, boria, thoria, phosphate, zinc oxide and silica. Alumina is a preferred binder.

The transalkylation catalyst also may contain an optional metal component. One preferred metal component may be a Group VIII (IUPAC 8-10) metal that includes nickel, iron, cobalt, and platinum-group metal. Of the platinum group, i.e., platinum, palladium, rhodium, ruthenium, osmium and iridium, platinum may be especially preferred. Another preferred metal component may be rhenium and it will be used for the general description that follows. This metal component may exist within the final catalytic composite as a compound such as an oxide, sulfide, halide, or oxyhalide, in chemical combination with one or more of the other ingredients of the composite. The rhenium metal component may be incorporated in the catalyst in any suitable manner, such as coprecipitation, ion-exchange, co-mulling or impregnation. The preferred method of preparing the catalyst involves the utilization of a soluble, decomposable compound of rhenium metal to impregnate the carrier material in a relatively uniform manner. Typical rhenium compounds which may be employed include ammonium perrhenate, sodium perrhenate, potassium perrhenate, potassium rhenium oxychloride, potassium hexachlororhenate (IV), rhenium chloride, rhenium heptoxide, perrhenic acid, and the like compounds. Preferably, the compound may be ammonium perrhenate or perrhenic acid because no extra steps may be needed to remove any co-contaminant species.

The transalkylation catalyst may optionally contain additional metal components along with those metal components discussed above or include additional metal components instead of those metal components in their entirety. Additional metal components of the catalyst include, for example, tin, germanium, lead, and indium and mixtures thereof. Catalytically effective amounts of such additional metal components may be incorporated into the catalyst by any means known in the art.

The resulting effluent from the reforming and transalkylation zones may be introduced into a vapor-liquid separator to provide a hydrogen-rich gaseous stream, which may optionally be recycled, and a liquid hydrocarbon stream. The effluent from the transalkylation zone may contain a minimum xylene content of at least 20% of the C6+ component in the effluent stream. The vapor-liquid separator optionally may be operated at a pressure of about 25 psig less than the reactor pressure in the reformer/transalkylation zones to account for transfer pressure drop. The liquid hydrocarbon stream from the vapor-liquid separator may be further fractionated in a benzene column to separate benzene from toluene, xylenes, and higher boiling aromatic compounds. The overhead stream removed from the benzene column contains primarily benzene and may be recovered as a benzene product stream or may optionally be recycled back into the stripper upstream of the main fractionation zone to maximize the yield of the most valuable xylenes. The overhead stream may contain about 95 to about 99.6% recovered benzene, containing about 200 mol-ppm to about 2 mol % toluene in the overhead stream. The benzene column can be operated at parameters to achieve about 95 to about 99.6% recovered benzene in the overhead stream. Alternatively, the benzene column overhead stream may be configured to make a high purity benzene product by removing the majority of benzenes from just below the top of the column, or overhead stream, and allowing the light components to go out the top stream overhead. This benzene stream could then be sent to a side rectifying column where a sharper cut of benzene can be withdrawn. Optionally, the liquid hydrocarbon stream from the vapor-liquid separator may be sent to the stripper upstream of the main fractionation zone, so that any heavy compounds formed in the transalkylation zone may be removed in the bottoms of the main fractionation zone.

The effluent from the benzene fractionation column, which may contain C7+ aromatics, may be sent to another fractionation column (i.e., a toluene column), which separates toluene from xylenes and higher boiling aromatic compounds. In a one aspect, the toluene may be recycled to the reforming zone to maximize the yield of the most valuable xylenes. In another aspect, the toluene may be recycled to the transalkylation zone, thus bypassing the reforming zone. In still another aspect, the toluene may be recovered and not recycled at all or a portion may be recovered and a portion may be recycled. The xylene contained in the overhead stream may be in the amount from about 500 to about 700 mol-ppm. The toluene in the bottom stream may comprise from about 500 to about 1000 mol-ppm in the xylene fraction of the bottoms. In the event that more benzene and toluene is desired at the expense of xylene production, they may be directed to product tanks. For example, if the operator wishes to produce additional high octane gasoline, the benzene/toluene net product flow rate would be increased and the overall xylene production would thereby decrease. This readily available feature affords a very flexible way to produce different product slates.

The effluent from the toluene column may then be sent to a final fractionation zone, such as a xylene column, to separate xylenes from other higher boiling compounds. The xylene product stream may be recovered as an overhead stream with a boiling point range from about 136° C. (277° F.) to about 143° C. (290° F.). The xylene mass flow recovered in the overhead stream is greater than the xylene mass flow before entering the transalkylation zone. The xylene recovered in the overhead stream of the xylene column is greater than the xylene recovered if the mid-cut naphtha stream were sent directly to the xylene column, hence bypassing the reforming and/or transalkylation zones. Furthermore, the xylene content in the overhead stream may be about 99%, with about 100 wt-ppm to about 1.5 wt % of C9+ aromatics.

The bottoms stream in the xylene column may be recovered as A10+ compounds and/or a side-cut bottoms stream comprising C9/C10 aromatics, which may be recycled and fed into the reforming zone and/or the transalkylation zone. The above-mentioned toluene overhead product from the toluene column may be combined with this side-cut stream from the xylene column and together fed into the reforming/transalkylation zone.

In another aspect, a LCO feedstock is supplied and first is introduced into a denitrification and desulfurization reaction zone together with hydrogen at hydrotreating reaction conditions, to provide the feedstock for the main fractionation zone discussed above. The LCO feedstock optionally may incorporate a liquid recycle stream from the main fractionation zone bottom fraction (i.e., the above-mentioned third fraction comprising ultra low sulfur diesel). In one aspect, the LCO feedstock is subject to mild hydrotreating/denitrification/desulfurization reaction conditions such as those utilizing a temperature from about 204° C. (400° F.) to about 482° C. (900° F.), a pressure from about 3.5 MPa (500 psig) to about 17.3 MPa (2500 psig), a liquid hourly space velocity of the fresh hydrocarbonaceous feedstock from about 0.1 to about 10 hr$^{-1}$ with a hydrotreating catalyst or a combination of hydrotreating catalysts. Other hydrotreating or other treatments of the LCO feedstocks may also be used prior to introduction of the feedstock to the main fractionation column. Alternatively, the LCO feedstock may be combined with hydrogen and heated prior to being introduced into the hydrocracking process, and the LCO feedstock may comprise a hydrocarbon stream containing C9+ hydrocarbons.

The term "hydrotreating" as used herein refers to processes wherein a hydrogen-containing treat gas is used in the presence of suitable catalysts which are primarily active for the removal of heteroatoms, such as sulfur and nitrogen. Suitable hydrotreating catalysts for use in treating the LCO feedstock may be any known conventional hydrotreating catalyst and may include those which are comprised of at least one Group VIII metal, preferably iron, cobalt and nickel, more preferably cobalt and/or nickel and at least one Group VI metal, preferably molybdenum and tungsten, on a high surface area support material, preferably alumina.

Other suitable hydrotreating catalysts include zeolitic catalysts, as well as noble metal catalysts where the noble metal may be selected from palladium and platinum. It is within the scope of the present invention that more than one type of hydrotreating catalyst may be used in the same reaction vessel. The Group VIII metal may typically be present in an amount ranging from about 2 to about 20 wt-%, preferably from about 4 to about 12 wt-%. The Group VI metal may typically be present in an amount ranging from about 1 to about 25 wt-%, preferably from about 2 to about 25 wt-%. Typical hydrotreating temperatures may range from about 204° C. (400° F.) to about 482° C. (900° F.) with pressures from about 3.5 MPa (500 psig) to about 17.3 MPa (2500 psig), preferably from about 3.5 MPa (500 psig) to about 13.9 MPa (2000 psig).

In accordance with one aspect of the present invention, the resulting effluent from the above-mentioned denitrification and desulfurization zone may be introduced into a hydrocracking zone, where the hydrotreated reactor is followed by a hydrocracking reactor. The hydrocracking zone may contain one or more beds of the same or different catalyst. In one aspect, the preferred hydrocracking catalysts may utilize amorphous bases or low-level zeolite bases combined with one or more Group VIII or Group VIB metal hydrogenation components. In another aspect, the hydrocracking catalyst may be selected from Y and Beta zeolite catalysts with Ni—Mo and Ni—W. In still another aspect, the hydrocracking zone may contain a catalyst which comprises, in general, any crystalline zeolite cracking base upon which may be deposited a minor proportion of a Group VIII metal hydrogenating component. Additional hydrogenation components may be selected from Group VIB for incorporation with the zeolite base.

The zeolite cracking bases are sometimes referred to in the art as molecular sieves and are usually composed of silica, alumina and one or more exchangeable cations such as sodium, magnesium, calcium, rare earth metals, etc. They are further characterized by crystal pores of relatively uniform diameter between about 4 and 14 angstroms. It is preferred to employ zeolites having a silica/alumina mole ratio between about 3 and 12. Suitable zeolites found in nature include, for example, mordenite, stillbite, heulandite, ferrierite, dachiardite, chabazite, erionite and faujasite. Suitable synthetic zeolites include, for example, the B, X, Y and L crystal types, e.g., synthetic faujasite and mordenite. The preferred zeolites are those having crystal pore diameters between about 8 and 12 angstroms, wherein the silica/alumina mole ratio is about 4 to 6. A prime example of a zeolite falling in the preferred group is synthetic Y molecular sieve.

The natural occurring zeolites are normally found in a sodium form, an alkaline earth metal form, or mixed forms. The synthetic zeolites are nearly always prepared first in the sodium form. In any case, for use as a cracking base it is preferred that most or all of the original zeolitic monovalent metals be ion-exchanged with a polyvalent metal and/or with an ammonium salt followed by heating to decompose the ammonium ions associated with the zeolite, leaving in their place hydrogen ions and/or exchange sites which have actually been decationized by further removal of water. Hydrogen or "decationized" Y zeolites of this nature are more particularly described in U.S. Pat. No. 3,130,006.

Mixed polyvalent metal-hydrogen zeolites may be prepared by ion-exchanging first with an ammonium salt, then partially back exchanging with a polyvalent metal salt and then calcining. In some cases, as in the case of synthetic mordenite, the hydrogen forms can be prepared by direct acid treatment of the alkali metal zeolites. The preferred cracking bases are those which are at least about 10 percent, and preferably at least about 20 percent, metal-cation-deficient, based on the initial ion-exchange capacity. A specifically desirable and stable class of zeolites are those wherein at least about 20 percent of the ion exchange capacity is satisfied by hydrogen ions.

The active metals employed in the preferred hydrocracking catalysts of the present invention as hydrogenation components may be those of Group VIII, i.e., iron, cobalt, nickel, ruthenium, rhodium, palladium, osmium, iridium and platinum. In addition to these metals, other promoters may also be employed in conjunction therewith, including the metals of Group VIB, e.g., molybdenum and tungsten. The amount of hydrogenating metal in the catalyst can vary within wide ranges. Broadly speaking, any amount between about 0.05 percent and about 30 percent by weight may be used. In the case of the noble metals, it is normally preferred to use about 0.05 to about 2 wt-%. The preferred method for incorporating the hydrogenating metal is to contact the zeolite base material with an aqueous solution of a suitable compound of the desired metal wherein the metal is present in a cationic form. Following addition of the selected hydrogenation metal or metals, the resulting catalyst powder may then be filtered, dried, pelleted with added lubricants, binders or the like, if desired, and calcined in air at temperatures of about 371° C. (700° F.) to about 648° C. (1200° F.) in order to activate the catalyst and decompose ammonium ions.

Alternatively, the zeolite component may first be pelleted, followed by the addition of the hydrogenating component and activation by calcining. The foregoing catalysts may be employed in undiluted form, or the powdered zeolite catalyst may be mixed and copelleted with other relatively less active catalysts, diluents or binders such as alumina, silica gel, silica-alumina cogels, activated clays and the like in proportions ranging between 5 and 90 wt-%. These diluents may be employed as such or they may contain a minor proportion of an added hydrogenating metal such as a Group VIB and/or Group VIII metal.

Additional metal promoted catalysts may also be utilized in the process of the present invention which comprises, for example, aluminophosphate molecular sieves, crystalline chromosilicates and other crystalline silicates. Crystalline chromosilicates are more fully described in U.S. Pat. No. 4,363,718.

The hydrocracking of the LCO feedstock in contact with a hydrocracking catalyst may be conducted in the presence of hydrogen and preferably at hydrocracking reactor conditions which include a temperature from about 232° C. (450° F.) to about 468° C. (875° F.), a pressure from about 3.5 MPa (500 psig) to about 20.8 MPa (3000 psig), a liquid hourly space velocity (LHSV) from about 0.1 to about 30 hr$^{-1}$, and a hydrogen circulation rate from about 84 normal m$^3$/m$^3$ (500 standard cubic feet per barrel) to about 4200 m$^3$/m$^3$ (25,000 standard cubic feet per barrel). In accordance with the present invention, the hydrocracking conditions may be selected on the basis of the LCO feedstock with the objective of the production of high purity xylene compounds and low sulfur diesel.

A hydrotreating/hydrocracking zone may contain one or more vessels or beds each containing one or more types of hydrotreating catalyst or hydrocracking catalyst. Optionally a liquid hydrocarbon stream may be recycled to the hydrotreating/hydrocracking zone, where the recycle stream may be introduced directly into a hydrocracking catalyst, or may be passed through a bed of hydrotreating catalyst and then contacted with the hydrocracking catalyst.

The resulting effluent from the hydrocracking zone may be introduced into a high pressure separator upstream of the main fractionation zone. The high pressure separator may produce a vaporous stream comprising hydrogen, hydrogen sulfide, and ammonia, and a liquid hydrocarbonaceous stream. The high pressure separator may preferably be operated at a temperature from about 149° C. (300° F.) to about 288° C. (550° F.) and a pressure from about 1.3 MPa (200 psig) to about 17.3 MPa (2500 psig). In another aspect, the resulting effluent from the hydrocracking zone may be introduced into a column operating at a lower pressure, such as atmospheric pressure, and operating without specific hydrogen stripping. The fractionator column may also produce a vapor stream comprising hydrogen, hydrogen sulfide and ammonia and a liquid stream comprising hydrocarbons.

The vapor stream comprising hydrogen, hydrogen sulfide, and ammonia may be treated to remove hydrogen sulfide and ammonia to provide a hydrogen-rich recycle gas. The vapor stream may be fed into an amine scrubber which separates the ammonia and hydrogen sulfide from the hydrogen-rich gas stream and the hydrogen-rich gas stream may then be sent to a recycle gas compressor and either fed to the hydrocracking/hydrotreating zone, if present, or to a second stage hydrogen compressor.

The resulting liquid hydrocarbon stream from the high pressure separator, a portion of which will be fed into the main fractionation zone downstream, may further be flashed in an additional high pressure separator, typically at a lower pressure than the initial high pressure separator to remove light gases that may then be sent to fuel. The liquid product may then be sent to a stripper column, where it may be steam stripped to remove propane and butane that may be sent to Liquid Petroleum Gas (LPG) recovery in an overhead stream of the stripper. The resulting stripper bottoms product contains gasoline, kerosene, and distillate boiling range material that may then be fed into the main fractionation column where the stripper bottoms product contains a significant amount of cyclic paraffins and aromatic compounds. The main fractionation column may then separate the stripper bottoms product into one or more main fraction streams by distillation, or, alternatively, into at least two or more fraction streams, as in the above-mentioned process.

In one aspect of the invention, make-up hydrogen gas may be fed to the above-mentioned hydrocracking/hydrotreating zone, if present, by means of a make-up compressor. A suitable make-up hydrogen stream would be any stream containing hydrogen at purity greater than about 90%, preferably greater than 99%, such as hydrogen from a PSA hydrogen recovery process. The make-up compressor may comprise a two-stage compressor, where the hydrogen enters the first stage compressor followed by the second stage compressor, before being introduced into the hydrocracking and/or hydrotreating zone. The make-up hydrogen may be combined with recycle hydrogen and process feed to generate the feed to the hydrotreating and/or hydrocracking reactors if used.

Downstream of the hydrotreating/hydrocracking zone, the hydrogen-rich gas from the top of the high pressure separator, upstream of the main fractionation zone, may preferably be amine treated to remove hydrogen sulfide and water washed to remove ammonia and sent to the hydrocracking zone recycle gas compressor which then may send the recycle hydrogen gas to two potential locations, namely, the second stage compressor and/or the hydrotreating/hydrocracking zone.

EXAMPLES

Example 1 below utilizes one aspect of the process of the present invention. As discussed above, in this process the feedstock to the main fractionation zone was separated to provide a naphtha stream having a boiling range from 71° C. (160° F.) to about 216° C. (420° F.), and the naphtha stream was subjected to the above-mentioned reformer and transalkylation zones. The effluent from the reformer/transalkylation zones was then separated and fractionated as mentioned above to provide a xylene stream.

In Example 2, the same feedstock as used in Example 1 was separated at the main fractionation zone into two streams, a naphtha stream (boiling range about 71° C. (160° F.) to about 216° C. (420° F.)) and a heavier hydrocarbon diesel boiling point range stream (boiling range above about 204° C. (400° F.)). The xylene boiling range material (boiling range about 136° C. (276° F.) to about 143° C. (290° F.)) is separated from the naphtha stream first and the remaining naphtha stream is then subject to the reforming/transalkylation zones after separation, therefore, initially the C8 stream is sent directly to the final fractionation column (i.e., sent to the xylene product column) and after separation of the xylene boiling range material the bottoms stream from the xylene column is recycled to the reforming/transalkylation zones.

As shown by the material balance data for the resulting process of Example 1 and Example 2, in Table 1 below, the process of this aspect of the invention provides a substantial increase in xylene purity without a significant decrease in xylene yield. Additionally, the purity of the C8 aromatics fraction from the process of Example 1, in terms of xylene product content (i.e. para-xylene, ortho-xylene, and meta-xylene), is increased relative to the purity of the C8 aromatics fraction from the process of Example 2, which includes a greater amount of ethylbenzene and/or other non-xylene C8 aromatics. (See e.g., A8 Xylene Product Purity, Table 1).

TABLE 1

Comparison of Material Balance for Examples 1 and 2

| Stream | Example 1 | Example 2 |
|---|---|---|
| Hydrocracked Naphtha Feed | 756.73 | 756.73 |
| Xylene Product | 283.89 | 308.42 |
| Benzene Product | 112.17 | 93.01 |
| Tatoray Stripper Overhead | 190.44 | 191.85 |
| Light Ends | 130.44 | 123.55 |
| Hydrogen | 2.44 | 0.51 |
| Diesel | 37.35 | 39.39 |
| Xylene Product Purity | 98 wt % | 79 wt % |
| A8 Xylene Product Purity | 99.8 wt % | 86 wt % |

DETAILED DESCRIPTION OF THE DRAWING

The drawing is a simplified process flow diagram of a preferred embodiment of the present invention. The drawing is intended to be schematically illustrative of the present invention and not to be a limitation thereof.

A liquid hydrocarbonaceous feedstock containing light cycle oil may be introduced into the process via line 1 and may be admixed with a hereinafter described hydrogen recycle stream provided by lines 48 and 51. The resulting admixture may be transported via line 2 and may be joined by a hereinafter described hydrogen-rich gaseous stream provided by line 46. This resulting admixture may be transported via line 3 and may be introduced into hydrotreating/hydrocracking zone 4. The resulting effluent from hydrotreating/hydrocracking zone 4 may be transported via line 5 and introduced into fractionation zone 6. A hydrogen-rich gaseous stream may be removed from fractionation zone 6 via line 9, and introduced into amine scrubber 41. Hydrogen sulfide and ammonia may be removed from amine scrubber 41 via line 42 and recovered.

A hydrogen-rich gaseous stream having a reduced concentration of hydrogen sulfide and ammonia may be removed from amine scrubber 41 and may be transported via line 47 to the recycle compressor 57. A liquid hydrocarbonaceous stream containing naphtha may be removed from fractionation zone 6 via line 7 and may be introduced into fractionation zone 8 via line 7 and flashed and introduced into fractionation zone 12 via lines 10 and 11. A propane and butane stream may be removed overhead from the fractionation zone 12 via line 59 and sent to LPG recovery. A liquid hydrocarbon stream may be removed from fractionation zone 12 via line 13 and introduced into main fractionation zone 14. A hydrocarbon stream containing ultra low sulfur diesel may be transported via line 17 and removed from fractionation zone 14. Another hydrocarbon stream containing C5/gasoline may be removed from fractionation zone 14 via line 15. Still another hydrocarbon stream containing C7+ and aromatic compounds is removed from fractionation zone 14 via lines 16 and 60 and passed to reforming/transalkylation zone 18.

A hydrogen-rich gas may be transported via line 39 and introduced when needed via lines 40 and 60 into reforming/transalkylation zone 18. A resulting effluent from the transalkylation portion of the reforming/transalkylation zone 18 may be transported via line 19 and introduced into vapor liquid separator 20. A hydrogen-rich gaseous stream may be removed from vapor liquid separator 20 via line 21 and may optionally be introduced into second stage makeup compressor 56 to produce a compressed hydrogen-rich gaseous stream carried via line 45 and introduced into hydrocracking zone 4 via lines 46 and 3.

A liquid hydrocarbonaceous stream containing transalkylated hydrocarbons may be removed from vapor liquid separator 20 via line 22 and introduced into benzene stripper 23. A stream containing benzene may be removed from benzene stripper 23 via line 24 and may optionally be transported via line 11 and optionally introduced into the fractionation zone 12. A liquid stream containing C7+ aromatic compounds may be removed from benzene stripper 23 via line 25 and introduced into toluene column 26. A stream containing toluene may be removed from toluene column 26 via line 27 and a portion may be transported via lines 30, 32, 34, 40 and 60 and introduced into the reformation/transalkylation zone 18 or alternatively a portion may be introduced into the transalkylation zone via lines 30, 31 and 33, thus bypassing the reforming zone. Another portion of the stream containing toluene may be removed from toluene column 26 via line 29, and recovered.

A liquid stream containing C8+ aromatic compounds may be removed from toluene column 26 via line 28 and introduced into fractionation zone 35. A stream containing xylenes may be removed from fractionation zone 35 via line 36 and recovered. A sidecut stream containing C9 and C10 aromatic compounds may be removed from fractionation zone 35 via line 38 and introduced via lines 38, 61, 34, 40, and 60 back into reforming/transalkylation zone 18. In an alternative embodiment, the sidecut stream containing C9 and C10 aromatic compounds in line 38 bypasses the reforming part of the reforming/transalkylation zone 18 and may be sent directly to the transalkylation part of reforming/transalkylation zone 18 via lines 38, 62, and 33. A hydrocarbon stream containing C10+ aromatic compounds may be removed from fractionation zone 35 via line 37.

A hydrogen-rich gaseous stream containing essentially no hydrogen sulfide is introduced via line 53 into first stage makeup compressor 54 and the resulting compressed hydrogen-rich gas is transported via line 55 to the second stage makeup compressor 56 and further transported via lines 45 and 3 and introduced into hydrotreating/hydrocracking zone 4. Additionally, a resulting compressed hydrogen-rich gaseous stream may be removed from recycle compressor 57 via line 58 and a portion may be carried via lines 48, 51, 2 and 3 and introduced into hydrotreating/hydrocracking zone 4 as hydrogen-rich recycle gas as hereinabove described and another portion may be carried via line 49 and may be joined by a hydrogen-rich gaseous stream provided via line 45 as described hereinabove and the resulting admixture may be transported via lines 46 and 3 and introduced into hydrocracking zone 4. A hydrogen-rich gaseous stream may be provided via lines 48 and 50 and optionally introduced into hydrocracking zone 4 bypassing the hydrotreating zone.

The foregoing description and drawing clearly illustrate the advantages encompassed by the process of the present invention and the benefits to be afforded with the use thereof.

The invention claimed is:

1. A process for the production of xylenes comprising:
   (a) passing a hydrocarbonaceous feed stream through a main fractionation zone to provide a naphtha stream having a xylene content greater than about 3% and boiling in the range from about 71° C. (160° F.) to about 216° C. (420° F.);
   (b) contacting at least an aliquot portion of the naphtha stream with a reforming catalyst in a reforming zone under reforming conditions to produce a reforming zone effluent comprising hydrogen and aromatic compounds;
   (c) contacting at least a portion of the reforming zone effluent with at least a transalkylation catalyst in a transalkylation zone under transalkylation conditions to produce a liquid hydrocarbonaceous transalkylation effluent and a gaseous stream comprising hydrogen, the transalkylation conditions selected so that the transalkylation effluent comprises xylenes without a substantial non-aromatic co-boiling content and having a xylene content greater than the xylene content of the naphtha stream before contacting the transalkylation catalyst; and
   (d) after the transalkylation zone, recovering xylenes to provide a xylene product having at least about 90 weight % xylene content.

2. The process of claim 1 wherein the naphtha stream is provided having at least about 80% cyclic component content and the naphtha stream further has a naphthene content of about 10% to about 40%, with less than about 20% paraffin content.

3. The process of claim 1 wherein the naphtha stream has a xylene content greater than about 5%.

4. The process of claim 1 wherein the naphtha stream has a xylene content greater than about 10%.

5. The process of claim 1 wherein the naphtha stream comprises primarily mid-cut naphthas, which include C7, C8, and C9 aromatic components, the mid-cut stream including substantially all of the C8 aromatic components of the naphtha stream.

6. The process of claim 1 wherein the xylene product has a total xylene content greater than about 98%.

7. The process of claim 1 wherein the process further includes directing a product stream from the transalkylation zone through a benzene and a toluene stripper to provide a stripped benzene product stream and a stripped toluene product stream, and wherein a portion of either or both stripped product streams is recycled back to the transalkylation zone.

8. The process of claim 1 wherein the process further comprises separating the feed stream in the main fractionation zone into a first fraction comprising primarily a light hydrocarbon stream boiling below about 126° C. (260° F.) and a third fraction comprising primarily an ultra low sulfur diesel stream boiling above about 193° C. (380° F.), wherein the naphtha stream is a second fraction.

9. The process of claim 8 wherein the first fraction comprises primarily a light hydrocarbon stream boiling below about 91° C. (195° F.).

10. The process of claim 1 wherein the reforming zone is a single reactor without reheat.

11. The process of claim 1 wherein the reforming conditions comprise a pressure from about 700 kPa (100 psig) to about 3.5 MPa (500 psig), a temperature from about 300° C. (572° F.) to about 565° C. (1049° F.), and a liquid hourly space velocity from about 0.2 to about 20 hr$^{-1}$.

12. The process of claim 1 wherein the transalkylation conditions comprise a temperature from about 200° C. (392° F.) to about 540° C. (1004° F.), a pressure from about 700 kPa (100 psig) to about 6 MPa (870 psig), and a liquid hourly space velocity from about 0.1 to about 20 hr$^{-1}$.

13. The process of claim 1 further comprising contacting a hydrocarbonaceous stream comprising C9+ hydrocarbons upstream of the main fractionation zone with a hydrocracking catalyst in a hydrocracking zone under hydrocracking conditions to produce a hydrocracking zone effluent comprising xylenes, where a portion of the effluent passes into the main fractionation zone.

14. The process of claim 1 further comprising bypassing at least a portion of the naphtha stream around the reforming zone and passing said portion of the naphtha stream to the transalkylation zone.

* * * * *